United States Patent [19]

Abraham et al.

[11] Patent Number: 5,049,695

[45] Date of Patent: Sep. 17, 1991

[54] ALLOSTERIC HEMOGLOBIN MODIFIERS

[75] Inventors: Donald J. Abraham, Midlothian; Ahmed Mehanna, Richmond; Ramnarayan Randad, Richmond; Mona Mahran, Richmond, all of Va.

[73] Assignees: Center for Innovative Technology, Herndon; Virginia Commonwealth University, Richmond, both of Va.

[21] Appl. No.: 478,848

[22] Filed: Feb. 12, 1990

[51] Int. Cl.$^5$ .............................................. C07C 271/00
[52] U.S. Cl. .......................................... 560/27; 560/30; 560/31; 560/32; 568/452; 568/455
[58] Field of Search ................ 560/31, 27, 30, 32; 562/452, 455

[56] References Cited

U.S. PATENT DOCUMENTS

| | | | |
|---|---|---|---|
| 4,482,571 | 11/1984 | Abraham et al. | 424/317 |
| 4,699,926 | 10/1987 | Abraham et al. | 514/563 |
| 4,704,402 | 11/1987 | Abraham et al. | 514/543 |
| 4,731,381 | 3/1988 | Abraham et al. | 514/571 |
| 4,731,473 | 3/1988 | Abraham et al. | 562/464 |
| 4,751,244 | 6/1988 | Abraham et al. | 514/563 |
| 4,887,995 | 12/1989 | Abraham et al. | 604/4 |

FOREIGN PATENT DOCUMENTS

| | | |
|---|---|---|
| 2432560 | 1/1976 | Fed. Rep. of Germany . |
| WO8810113 | 12/1988 | World Int. Prop. O. . |
| WO8912622 | 12/1989 | World Int. Prop. O. . |

OTHER PUBLICATIONS

Chemical Abstract, vol 84, No. 121481a, "Phenoxyalkanoic Acid Derivatives", abstract from DE 2,432,560.
Perutz, "Mechanisms of Cooperativity and Allosteric Regulation in Proteins", Quarterly Review of Biophysics, 22:2 (1989), pp. 139, 163 and 164.
Lalezari et al., "LR16, A Compound with Potent Effects on the Oxygen Affinity of Hemoglobin, on Blood Cholesterol, and on Low Density Lipoprotein", Proc. Natl. Acad. Sci. (U.S.A.) 85 (1988) pp. 6117–6121.
Chemical Abstracts, 25-Noncondensed Aromatics, vol. 79 (1973), pp. 417, No. 1843k which identifies German Patent 2,149,070.

Perutz, "Bezafibrate Lowers Oxygen Affinity of Hemoglobin", The Lancet, Oct. 15, 1983, pp. 881–882.
Pertuz et al., "Hemoglobin as a Receptor of Drugs and Peptides: X-Ray Studies of the Stereochemistry of Binding", J. Amer. Chem. S., vol. 108, (1986), pp. 1064–1078.
Abraham, et al., "Design, Synthesis, and Testing of Potential Antisickling Agents. 4. Structure-Activity Relationships of Benzyloxy and Phenoxy Acids", J. Med. Chem., vol. 27, (1984) pp. 967–978.
Abraham et al., "Design Synthesis, and Testing of Potential Antisickling Agents. 7. Ethacrynic Acid Analogues", J. Med. Chem., vol. 32, (1989), pp. 2460–2467.
Zijlstra et al., "Standardization of Hemoglobinometry. 1. The Extinction Coefficient of Hemiglobincyanide", Clinica Chimica Acta, vol. 5, (1960), pp. 719–726.
Zijlstra et al., "Spectrophotometry of Haemoglobin: The Standard Haemiglobin Cyanide Method and After", J. Clin. Chem. Biochem., vol. 19, (1981), pp. 521–523.
Dozy et al., "Studies on the Heterogeneity of Hemoglobin. XIII. Chromotagraph of Various Human and Animal Hemoglobin Types on DEAE-Sephadex", J. Chrom., vol. 32, (1968) pp. 723–726.
Aminco Hem-O-Scan TM Laboratory Manual.
Hemoglobin Structure/Function, lecture by Dr. Abraham on Oct. 3, 1990.

*Primary Examiner*—Jose G. Dees
*Assistant Examiner*—Porfirio Nazario
*Attorney, Agent, or Firm*—Whitham & Marhoefer

[57] ABSTRACT

Allosteric hemoglobin modifier compounds having the general formula

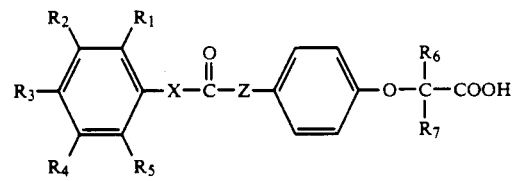

wherein X and Z may be $CH_2$, NH or O.

3 Claims, 2 Drawing Sheets

ALLOSTERIC HEMOGLOBIN MODIFIERS

BACKGROUND OF THE INVENTION

1. Field of the Invention

The invention relates to a new class of compounds that are useful for the allosteric modification of hemoglobin. In particular the invention relates to a family of new compounds having the general structural formula set forth in FIG. 1 of the drawings. In the formula of FIG. 1, X and Z may each be $CH_2$, NH or O.

2. The Prior Art Scenario

Hemoglobin is a tetramer with two $\alpha$ and two $\beta$ subunits. Moreover, hemoglobin is an allosteric protein in equilibrium between two allosteric structures; the deoxy or T state with low oxygen affinity and the oxy or R state with high oxygen affinity. In the past proposals have been made for attempting to influence the allosteric equilibrium of hemoglobin using synthetic compounds. These attempts have been based on the fact that high affinity hemoglobin is thought to be beneficial in resolving problems associated with the deoxy form, as in the case of sickle cell anemia. On the other hand, low affinity hemoglobin is believed to have general utility in a variety of disease states where tissues suffer from low oxygen tension, such as ischemia and cancer.

In the past, a number of chemical compounds have been identified as having utility in the allosteric regulation of hemoglobin and other proteins. For example, see Perutz, "Mechanisms of Cooperativity and Allosteric Regulation in Proteins", *Quarterly Reviews of Biophysics* 22, 2 (1989), pp. 163-164; and Lalezari et al., "LR16, a compound with potent effects on the oxygen affinity of hemoglobin on blood cholesterol, and on low density lipoprotein", *Proc. Natl. Acad, Sci, USA* 85 (1988), pp. 6117-6121. Structurally similar compounds are disclosed in German patent Publication No. 2,149,070 but without any indication of a potential for allosteric hemoglobin modification. As in other related fields the search continues for drugs that can be conveniently prepared and which provide optimum therapeutic results.

SUMMARY OF THE INVENTION

The present invention provides a family of new compounds that are useful as allosteric hemoglobin modifiers. The compounds of the invention have the general formula illustrated in FIG. 1 of the drawings, wherein X and Z may each be $CH_2$, NH or O. In the compounds of the invention, when X is $CH_2$, Z may be NH; when X is NH, Z may be either $CH_2$ or O; and when X is O, Z may be NH. In accordance with the present invention, $R_1$, $R_2$, $R_3$, $R_4$ and $R_5$ may be halogen atoms or $C_1$, $C_2$ or $C_3$ alkyl or substituted alkyl groups, and these moieties may be the same or different. Moreover, $R_6$ and $R_7$ may be H or $CH_3$ and these moieties also may be the same or different.

DETAILED DESCRIPTION OF THE INVENTION

The present invention provides a family of organic compounds capable of functioning to allosterically modify hemoglobin and other allosteric proteins. Thus, the compounds of the invention should be valuable as antischemic agents, as enhancers for X-ray radiation in cancer therapy, as antilipidemic agents, in preparing blood substitutes and in blood storage.

Figure 1:
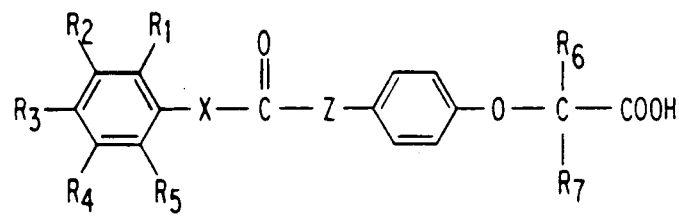
FIGS. 1 illustrates the general structural formula of the new compounds which embody the principles and concepts of the invention.

The compounds of the invention have the general structural formula illustrated in FIG. 1 of the drawings wherein X and Z may each be either $CH_2$, NH or O.

In accordance with the invention, and with specific reference to FIG. 1, when X is $CH_2$, Z may be NH; when X is NH, Z may be either $CH_2$ or O; and when X is O, Z may be NH.

In the preferred form of the invention, and again with reference to FIG. 1, $R_1$, $R_2$, $R_3$, $R_4$ and $R_5$ may be H, halogen or a substituted or unsubstituted $C_1$, $C_2$ or $C_3$ alkyl group, and these moieties may be the same or different. Additionally, $R_6$ and $R_7$ may preferably be H or $CH_3$ and these moieties also may be the same or different.

Figure 2A:
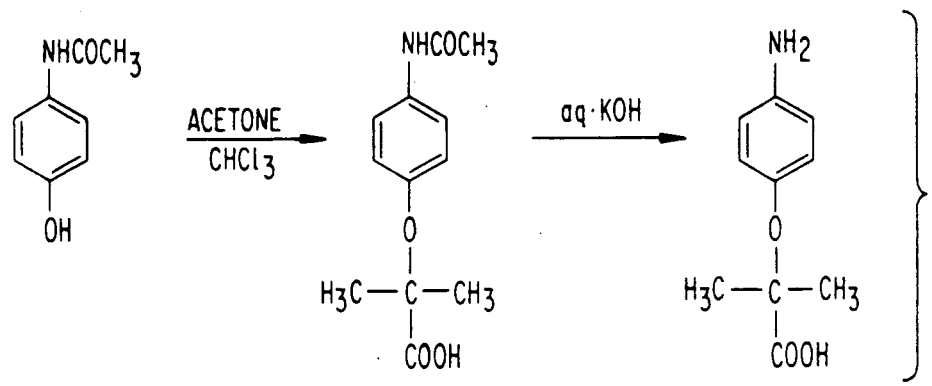
FIGS. 2A and 2B illustrate structural formulas of precursor compounds and reaction schemes for preparing compounds that are useful as intermediates for synthesizing a first group of compounds embodying the concepts and principles of the invention.
Figure 2B:
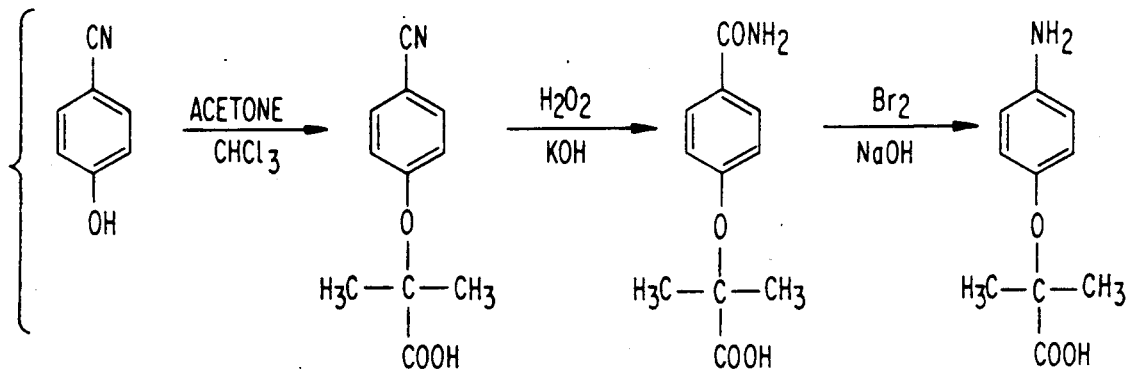
Figure 2C:
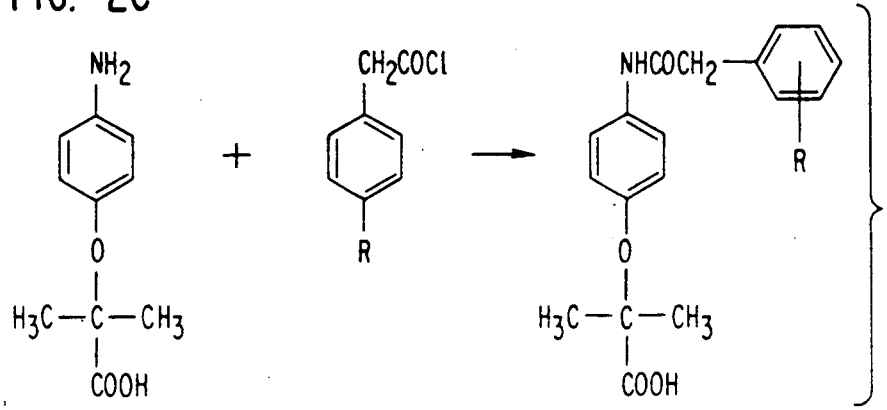
FIG. 2C illustrates structural formulas and a reaction scheme utilizing the intermediates of FIGS. 2A and 2B for preparing said first group of compounds.
Figure 3:
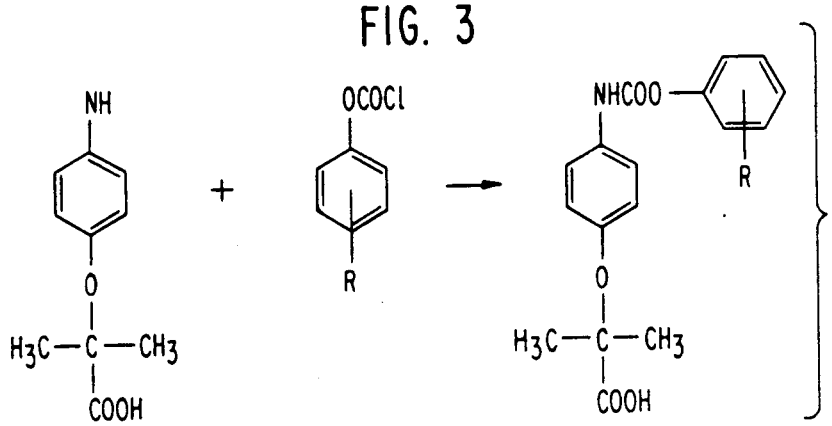
FIG. 3 illustrates structural formulas and a reaction scheme useful for preparing a second group of compounds embodying the concepts and principles of the invention.
Figure 4:
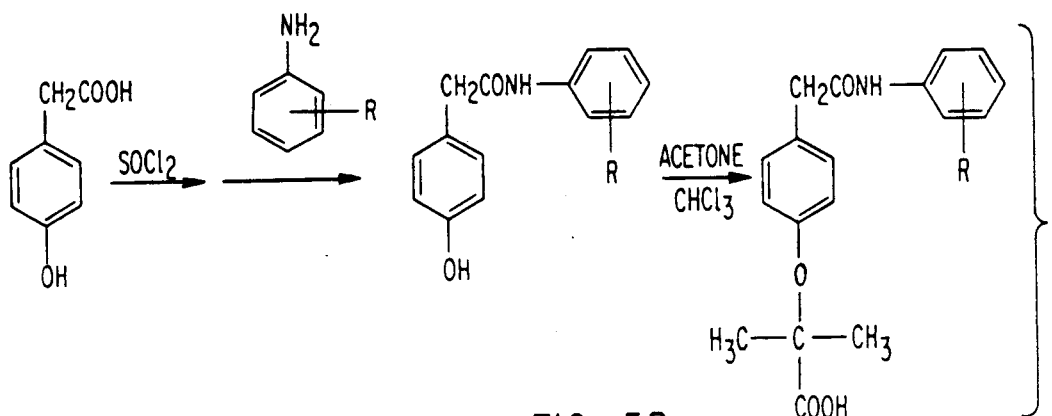
FIG. 4 illustrates structural formulas and a reaction scheme useful for preparing a third group of compounds embodying the concepts and principles of the invention.
Figures 5A, 5B:
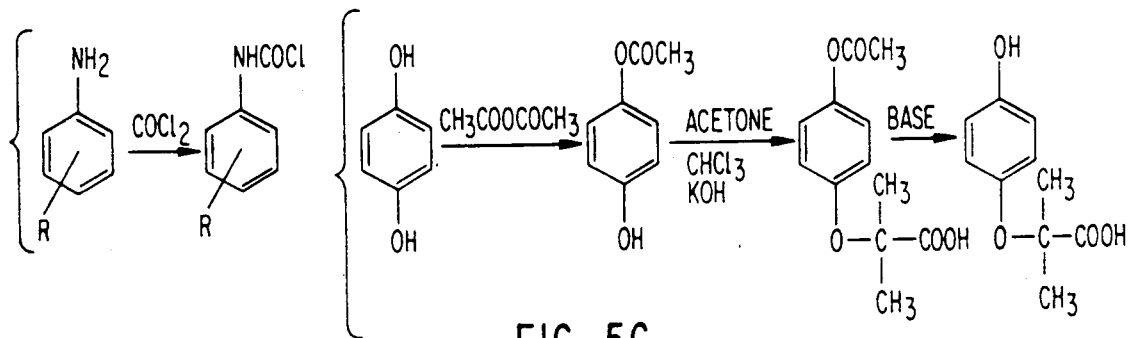
FIGS. 5A and 5B illustrate structural formulas of precursor compounds and reaction schemes for preparing compounds that are useful as intermediates for synthesizing a fourth group of compounds embodying the concepts and principles of the invention.
Figure 5C:
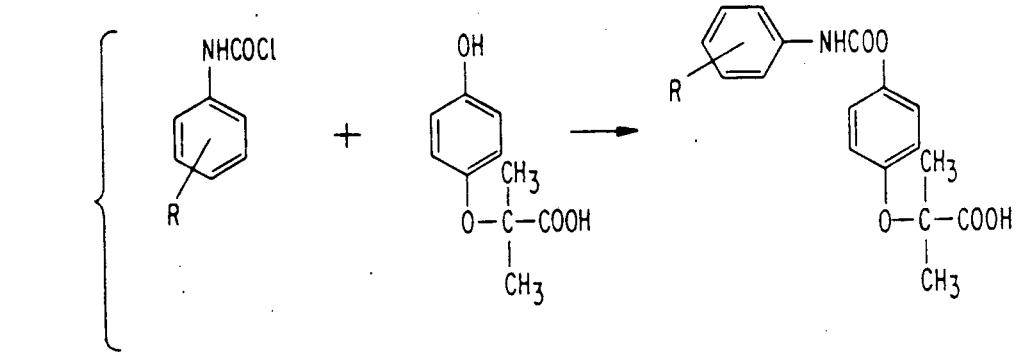
FIG. 5C illustrates structural formulas and a reaction scheme utilizing the intermediates of FIGS. 5A and 5B for preparing said fourth group of compounds.

The compounds of the invention may conveniently be classified into four distinct groupings as follows:

Group I: 2-[4-((aryl)acetamido)phenoxy]-2-methyl propionic acids having a structural formula as illustrated in FIG. 2C of the drawings;

Group II: 2-[4-(((aryloxy)carbonyl)amino)phenoxy]-2-methyl propionic acids having a structural formula as illustrated in FIG. 3;

Group III: 2-[4-((((aryl)amino)carbonyl)methyl)-phenoxy]-2-methyl propionic acids having a structural formula as illustrated in FIG. 4; and Group IV: 2-[4-(((arylamino)carbonyl)oxy)phenoxy]-2-methyl propionic acids having a structural formula as illustrated in FIG. 5C.

EXAMPLE 1

FIG. 2A illustrates a reaction scheme for preparing 2-(4-aminophenoxy)-2-methyl propionic acid, a compound that is useful as a precursor in the preparation of Group I compounds. In accordance with the scheme of FIG. 2A, 8 g (0.2 mol) of pulverized sodium hydroxide is added to a suspension of 5.28 g (0.035 mol) of p-acetaminophenol in 23 g (0.4 mol) of acetone. The reaction mixture is stirred at room temperature for ½ hour. Subsequently, 3.58 g (0.03 mol) of chloroform is added dropwise over the course of 30 minutes. The reaction mixture is stirred overnight at room temperature and acetone is removed under vacuum. The residue is dissolved in water (10 ml), followed by acidification with 37% hydrochloric acid to produce a pale yellow precipitate of 2-(4-acetaminophenoxy)-2-methyl propionic acid (5 g, 60% yield), crystallized from methanol, mp 69°–71° C.

$^1$H NMR: (CD30D) δ 7.1(m,4H) Ar$\underline{H}$, 2.05 (s,3H) C$\underline{H}_3$, 1.45 (s,6H) 2C$\underline{H}_3$ 1.18 g (0.005 mol) of the 2-(4-acetaminophenoxy)-2-methyl propionic acid is boiled in 10% KOH (60 ml) for ½ hour. The solution is then cooled and acidified with acetic acid to yield 0.6 g (62% yield) of 2-(4-aminophenoxy)-2-methyl propionic acid as a yellowish white powder, mp 214°–16° C.

$^1$H NMR: (DMSOd6+TMS) δ 6.6 (m,4H)Ar$\underline{H}$, 1.35 (s,6H) 2C$\underline{H}_3$

EXAMPLE 2

FIG. 2B illustrates another reaction scheme for preparing 2-(4-aminophenoxy)-2-methyl propionic acid. In accordance with the scheme of FIG. 2B, 8 g of potassium hydroxide is dissolved in 32 ml of water and the resultant KOH solution is admixed with 280 ml of 3% hydrogen peroxide. 11.3 g (0.058 mol) of 2-(4-cyanophenoxy)-2-methyl propionic acid is slowly added to the KOH/H$_2$O$_2$ solution and the reaction mixture is stirred for about one hour until the exotherm and evolution of gas has ceased. The mixture is then cooled and acidified with concentrated hydrochloric acid. The 2-[4-(carboxamido) phenoxy]-2-methyl propionic acid product is obtained as a white solid (9.8 g, 79% yield). The product is crystallized from ethanol to produce pure white crystals, mp 202°–4° C.

5.57 g (0.025 mol) of the 2-[4-(carboxamido)phenoxy]-2-methyl propionic acid is added gradually with stirring to 100 ml of an ice cold aqueous solution containing 4.4 g (0.025 mol) of bromine and 11 g (0.25 mol) of sodium hydroxide. The solution thus obtained is warmed at 75° C. for ½ hour. After cooling, the solution is acidified with acetic acid giving the desired 2-(4-aminophenoxy)-2-methyl propionic acid product as 4.0 g (81% yield) of a white precipitate, mp 214°–16° C. The compound is identical with the product prepared in Example 1.

EXAMPLE 3

FIG. 2C illustrates a general reaction scheme for preparing the Group I 2-[4-(arylacetamido)phenoxy]-2-methyl propionic acids. In accordance with the illustrated scheme, 1 g (0.005 mol) of 2-(4-aminophenoxy)-2-methyl propionic acid is dissolved with stirring in 10 ml of water containing 0.41 g (0.1 mol) of NaOH. To this solution, 0.79 g (0.005 mol) of phenyl acetyl chloride in 5 ml of THF is gradually added over a period of about 15 minutes. After the addition is complete the pH of the reaction mixture should be alkaline (if not a few drops of 2N NaOH is added to assure alkalinity). The reaction mixture is continuously stirred for 1 hour. Thereafter the THF is evaporated in vacuo, and the solution is then diluted with 5 ml water and acidified with concentrated hydrochloric acid. The product is extracted with ethyl ether (2×20 ml), washed with water (3×20 ml), and then dried over anhydrous MgSO$_4$. Upon addition of petroleum ether to the ether solution, 0.9 g (56% yield) of the 2-[4-(phenylacetamido)phenoxy]-2-methyl propionic acid product precipitates as a pale brown solid, mp 173°–5° C.

$^1$H NMR: (DMSOd6) 10 (s, 1H) COO$\underline{H}$, 7.5–6.7 (m, 9H) Ar$\underline{H}$, 3.55 (s, 2H) C$\underline{H}_2$, 1.4 (s, 6H), 2C$\underline{H}_3$ Anal: C$_{18}$H$_{19}$NO$_4$. Calc: C 69.00, H 6.07, N 4.47. Found: C 68.86, H 6.14, N 4.42.

EXAMPLE 4

In this Example the procedure of Example 3 is followed exactly except that 0.005 mol of 4-chlorophenyl acetyl chloride is substituted for the phenyl acetyl chloride. In this case the product (57% yield) is 2-[4-(p-chlorophenyl)acetamido)phenoxy]-2-methyl propionic acid, mp 168°–71° C.

$^1$H NMR: (DMSOd6) δ 10 (s, 1H) COO$\underline{H}$, 7.6–6.7 (m, 8H) Ar$\underline{H}$, 3.6 (s, 2H) C$\underline{H}_2$, 1.4 (s, 6H), 2C$\underline{H}_3$ Anal: C$_{18}$H$_{18}$NO$_4$Cl. Calc: C 62.15, H 5.17, N 4.02, Cl 10.12. Found: C 62.16, H 5.25, N 3.98, Cl 10.25.

The 4-chlorophenyl acetyl chloride for the foregoing synthesis is prepared by heating to reflux a suspension of 1 g (0.006 mol) of 4-chlorophenyl acetic acid in 1.07 g (0.009 mol) of thionyl chloride with stirring for 1 hour. After cooling, excess thionyl chloride is evaporated under vacuum to present the 4-chlorophenyl acetyl chloride product as a yellow oil (1 g, 83% yield).

EXAMPLE 5

FIG. 3 illustrates a general reaction scheme for preparing the Group II 2-[4-(((aryloxy)carbonyl)amino)-phenoxy]-2-methyl propionic acids. In accordance with the illustrated scheme, a solution consisting of 0.15 g (0.001 mol) of phenyl chloroformate in 3 ml THF is gradually added to an ice cold solution containing 0.3 g (0.001 mol) of 2-(4-amino phenoxy)-2-methyl propionic acid and 0.17 g (0.002 mol) of sodium bicarbonate in 10 ml of water (10 ml). The reaction mixture is stirred for ½ hour at 0° C., followed by stirring for 1 hour at room temperature. The THF is removed in vacuo and 10 ml of water is added. Then the reaction mixture is acidified with concentrated hydrochloric acid and extracted with ethyl ether (2×20 ml). The ether solution is washed with water (3×20 ml) and dried over anhydrous MgSO$_4$. The desired product,2-[4-((((phenyl)oxy)carbonyl)amino)phenoxy]-2-methyl propionic acid, is precipitated from the ether solution by addition of petroleum ether as a white solid, 0.15 g (31% yield), mp 183°–5° C.

$^1$H NMR: (DMSOd6) δ 10 (s,1H) COO$\underline{H}$, 7.55–6.75 (m,9H) Ar$\underline{H}$, 1.4 (s, 6H) 2C$\underline{H}_3$ Anal: C$_{17}$H$_{17}$O$_5$N. Calc: C 64.76, H 5.39, N 4.44. Found: C 64.65,H 5.45, N 4.43.

EXAMPLE 6

In this example the procedure for Example 5 is followed exactly except that 0.001 mol of 4-chlorophenyl chloroformate is substituted for the phenyl chloroformate. In this case the 2-[4-((((p-chlorophenyl)oxy)carbonyl)amino)phenoxy]-2-methyl propionic acid product is obtained as a white precipitate, 0.15 g (28% yield), mp 179°–82° C.

$^1$H NMR: (DMSOd6+TMS) δ 7.6–6.8 (m, 8H) Ar$\underline{H}$, 1.4 (s,6H) 2C$\underline{H}_3$ Anal: C$_{17}$H$_{16}$O$_5$NCl. Calc: C 58.36, H 4.57, Cl 10.15. Found: C 58.16, H 4.68, Cl 10.35.

EXAMPLE 7

FIG. 4 illustrates a general reaction scheme for preparing the Group III compounds of the invention. In accordance with the illustrated scheme, 5.2 g (34 mmol) of p-hydroxy phenyl acetic acid (HPAA) is heated to reflux with an excess of thionyl chloride for ½ hour. The reaction mixture is then cooled and excess $SOCl_2$ is removed under vacuum. The residue is reacted for 2 hours with 6.3 g (68 mmol) of aniline in 50 ml of refluxing xylene. The reaction mixture is then cooled, washed with dilute HCl, water and brine and extracted with aqueous 2N NaOH. The combined alkali layer is washed with ether, cooled and acidified to provide 7 g of solid N-phenyl-4-hydroxybenzyl amide ($C_{14}H_{12}NO_2$) as an intermediate product (90% yield), mp 138° C. The intermediate product is recrystallized from a 1:2 mixture of acetone and petroleum ether and 1.13 g (5 mmol) portion is o-alkylated for 12 hours using the procedure of Example 1 with 20 ml acetone, 2.75 g NaOH and 1.25 ml $CHCl_3$. The final product is 2-[4-((((phenyl)amino)-carbonyl)methyl)phenoxy]-2-methyl propionic acid ($C_{18}H_{19}NO_4$), 1.2 g (76% yield), mp 198° C.

EXAMPLE 8

The procedure of Example 7 is repeated using 8.6 g (68 mmol) of 4-chloroaniline rather than the aniline. In this case, the intermediate product is N-(4-chlorophenyl)-4-hydroxy benzylamide ($C_{14}H_{12}ClNO_2$), 7.5 g (84% yield), mp 163° C. 1.3 g of the intermediate product is o-alkylated to produce 2-[4((((4-chlorophenyl)amino)carbonyl)methyl)phenoxy]-2-methyl propionic acid ($C_{18}H_{18}ClNO_4$), 0.86 g (50% yield), mp 196° C.

EXAMPLE 9

The procedure of Example 7 is repeated using 2.6 g (17 mmol) of the HPAA and using 5.67 g (35 mmol) of 3,4-dichloro aniline rather than the aniline. In this case the intermediate product is N-(3,4-dichlorophenyl-4-hydroxy benzylamide ($C_{14}H_{11}Cl_2NO_2$). 1.48 g (5 mmol) of the intermediate is o-alkylated to produce 2-[4-(((3,4-dichlorophenyl)amino) carbonyl)methyl)phenoxy]-2-methylpropionic acid ($C_{18}H_{17}Cl_2NO_4$), 0.76 g (40% yield), mp 174° C.

EXAMPLE 10

The procedure of Example 7 is repeated using 2.6 (17 mmol) of the HPAA and using 5.7 g (35 mmol) of 3,5-dichloro aniline rather than the aniline. In this case the intermediate product is N-(3,5-dichlorophenyl-4-hydroxy benzylamide ($C_{14}H_{11}Cl_2NO_2$). 1.48 g (5 mmol) of the intermediate is o-alkylated to produce 2-[4-((((3,5-dichlorophenyl)amino)carbonyl)methyl)phenoxy]-2-methyl propionic acid ($C_{18}H_{17}Cl_2NO_4$), 0.8 g (42% yield), mp 138° C.

EXAMPLE 11

The procedure of Example 7 is repeated using 0.95 g (6 mmol) of the HPAA, using 2.6 g (12 mmol) of 3,4,5-trichloro aniline rather than the aniline, and using 25 ml of refluxing xylene. In this case the intermediate product is N-(3,4,5-trichlorophenyl)-4-hydroxy benzylamide. 0.50 g (1.5 mmol) of the intermediate product is o-alkylated using 10 ml acetone, 0.82 g NaOH and 0.37 ml $CHCl_3$ to produce 2-[4-((((3,4,5-trichlorophenyl)amino)carbonyl)methyl)phenoxy]-2-methyl propionic acid ($C_{18}H_{16}Cl_3NO_4$), 0.27 g (43% yield), mp 160° C.

EXAMPLE 12

The procedure of Example 7 is repeated using 5.04 g (32 mmol) of the HPAA, using 6 ml (64 mmol) of 4-fluoro aniline rather than aniline, and using 25 ml of refluxing xylene. In this case the intermediate product is N-(4-fluorophenyl)-4-hydroxy benzylamide. 1.22 g (5 mmol) of the intermediate product is o-alkylated to produce 2-[4-((((4-fluorophenyl)amino)carbonyl)methyl)phenoxy]-2-methyl propionic acid ($C_{18}H_{18}FNO_4$), 0.74 g (45% yield), mp 198° C.

EXAMPLE 13

The procedure of Example 7 is repeated using 5.04 (32 mmol) of the HPAA, using 8.05 ml (64 mmol) of 4-trifluoromethyl aniline rather than aniline, and using 25 ml of refluxing xylene. In this case the intermediate product is N-(trifluoromethylphenyl)-4-hydroxy benzylamide. 1.5 g (5 mmol) of the intermediate is used to produce 2-[4-((((4-trifluoromethylphenyl)amino)carbonyl)methyl)phenoxy]-2-methyl propionic acid ($C_{19}H_{18}F_3NO_4$), 0.85 g (44% yield), mp 197° C.

EXAMPLE 14

The procedure of Example 7 is repeated using 5.04 (32 mmol) of the HPAA, using 8 g (65 mmol) of 4-methyl aniline rather than aniline, and using 25 ml of refluxing xylene. In this case the intermediate product is N-(4-methylphenyl)-4-hydroxy benzylamide. 1.2 g (5 mmol) of the intermediate is used to produce 2-[4-((((4-methylphenyl)amino)carbonyl)methyl)phenoxy]-2-methyl propionic acid ($C_{19}H_{21}NO_4$), 0.98 g (65% yield), mp 164° C.

EXAMPLE 15

The procedure of Example 7 is repeated using 3.26 (21 mmol) of the HPAA, using 5.3 ml (42 mmol) of 3,5-dimethyl aniline rather than aniline, and using 25 ml of refluxing xylene. In this case the intermediate product is N-(3,5-dimethylphenyl)-4-hydroxy benzylamide. 1.27 g (5 mmol) of the intermediate is used to produce 2-[4-((((3,5-dimethylphenyl)amino)carbonyl)methyl)-phenoxy]-2-methyl propionic acid ($C_{20}H_{23}NO_4$), 1.15 g (68% yield), mp 85° C.

EXAMPLE 16

The procedure of Example 7 is repeated using 5.04 (32 mmol) of the HPAA, using 10 ml (64 mmol) of 4-isopropyl aniline rather than aniline, and using 25 ml of refluxing xylene. In this case the intermediate product is N-(4-isopropylphenyl)-4-hydroxy benzylamide. 1.34 g (5 mmol) of the semi-solid, thick viscous liquid intermediate is used to prepare 2-[4-((((4-isopropylphenyl)amino-)carbonyl)methyl) phenoxy]-2-methyl propionic acid ($C_{21}H_{25}NO_4$), 1.1 g (62% yield), mp 141° C.

With reference to FIGS. 5A, 5B and 5C, a scheme is illustrated for preparing Group IV compounds. In accordance with FIG. 5A, aniline or aniline derivatives may be reacted with phosgene to obtain the carbamoyl chloride. In accordance with FIG. 5B, hydroquinone may be monoacetylated using acetic anhydride. The product is o-alkylated using acetone, $CHCl_3$ and KOH and then hydrolyzed using a base. The products of the reactions of FIGS. 5A and 5B may then be reacted according to the reaction of FIG. 5C to produce the Group IV 2-[4-(((arylamino)carbonyl)oxy)phenoxy)]-2-methyl propionic of the invention.

To test the compounds of the invention for physiological activity, human blood was obtained either from Central Blood Bank, Richmond, Va. (donors homozygous for Hba) or Howard University, Washington, D.C. (donors homozygous for HbS). Extraction, chromatography, and characterization of isolated hemoglobins were identical to that described by Dozy and Huisman, J. of Chromatography, vol. 32, p. 723 (1968) and in The Chromatography of Hemoglobin, H. J. Schroeder and D. H. J. Huisman, Ed. Marcel Dekker Inc. N.Y. (1980). The purity of separate HBA or HbS was determined by gel electrophoresis, using a Gelman semimicroelectrophoresis chamber. The concentration of hemoglobin was determined by the cyanmethemoglobin method (Zijlstra, Clin. Chem. Acta. vol. 5, pp. 719-726 (1960), Z ijlstra and Van Kamper, J. Clin. Chem. Clin. Biochem., vol. 19, p. 521 (1981)). All purified hemoglobin solutions were stored in liquid nitrogen. The reagents and buffers were purchased from the following sources: Fischer Scientific, Sigma Chemical Company, and Pharmacia and Research Chemicals, Inc.

Oxygen equilibrium curves were determined on a Minco HEM-O-SCAN oxygen dissociation analyzer (Travenol Laboratories). HbA was prepared as follows: 20 ml of whole blood from a nonsmoking donor (blood bank, Richmond, Va.) was drawn into a heparinized vacutainer. The blood was immediately packed in ice (to prevent MetHb formation) and then centrifuged (10 minutes at 2500 rpm) to separate the plasma and buffy coat from the packed erythrocytes. After centrifugation was completed, the plasma and buffy coat were removed by aspiration and the cells washed three times with 0.9% NaCl (40 mg of EDTA/L) and then once with 1.0% NaCl (40 mg of EDTA/L). The cells were lysed by the addition of one to two volumes of deionized water containing 40 mg of EDTA/L. This was allowed to stand for 30 minutes with occasional mixing before being centrifuged for 2 hours at 10,000 rpms at 4° C. The supernatant was decanted into 50 ml tubes and NaCl (50 mg/ml of Hb supernatant) was added, mixed and centrifuged at 10,000 rpms at 4° C. for 2 hours to remove the remaining cell stroma. The supernatant was further purified by either gel filtration with Sephadex G-25 or dialysis against pH 8.6 tris buffer (50 mM, containing 40 mg of EDTA/L). The sodium chloride free hemoglobin solution was chromatographed on DEAE-Sephacel ion-exchange resin (Sigma) preequilibrated with Tris buffer pH 8.6. After elution of the A2 hemoglobin fraction by Tris buffer (pH 8.6, 50 mM, containing EDTA/L), the HbA fraction was then eluted with pH 8.4 Tris buffer. The pure HbA fraction (identified by electrophoresis) was concentrated using a Schleicher and Schuell collodion bag apparatus (Schleicher and Schuell, Inc.) with HEPES buffer (150 mM, pH 7.4) as the exchange buffer. The hemoglobin concentration was then determined using the cyanomethemoglobin method (as mentioned before). The hemoglobin concentration at this point was usually found to be around 35G% (approximately 5.5 mM). Less than 5% methemoglobin was noted even after several days at 4° C.

All compounds were mixed with one equivalent NaHCO$_3$, then dissolved in the HEPES buffer to give 20 mM solutions. Just prior to running the oxygen equilibrium curve, the Hb and the drug were mixed in a 1:1 ratio (50 ul of Hb+50 ul of drug) to give 2.75 mM Hb with a drug concentration of 10 mM. The control was prepared by the addition of 50 ul of Hb to 50 ul of the HEPES. The results are tabulated in Table 1.

TABLE 1

The P$_{50}$ values of the Synthesized Compounds

| Example No. | R$_1$ | R$_2$ | R$_3$ | R$_4$ | R$_5$ | X | Z | No. of Runs | P$_{50}$ (Control) | *P$_{50}$ | *P$_{50}$/P$_{50}$C |
|---|---|---|---|---|---|---|---|---|---|---|---|
| 3 | H | H | H | H | H | CH$_2$ | NH | 1 | 18 | 23 | 1.27 |
| 4 | H | H | Cl | H | H | CH$_2$ | NH | 3 | 18 | 47.8 | 2.65 |
| 5 | H | H | H | H | H | O | NH | 2 | 18 | 26.5 | 1.47 |
| 6 | H | H | Cl | H | H | O | NH | 1 | 19 | 34 | 1.78 |
| 7 | H | H | H | H | H | NH | CH$_2$ | 1 | 11 | 36 | 3.27 |
| 8 | H | H | Cl | H | H | NH | CH$_2$ | 2 | 18 | 60 | 3.33 |
| 9 | H | Cl | Cl | H | H | NH | CH$_2$ | 1 | 13 | 39 | 3.00 |
| 10 | H | Cl | H | Cl | H | NH | CH$_2$ | 3 | 19 | 75 | 3.94 |
| 11 | H | Cl | Cl | Cl | H | NH | CH$_2$ | 2 | 11 | 27 | 2.45 |
| 12 | H | H | F | H | H | NH | CH$_2$ | 1 | 18 | 43 | 2.38 |
| 13 | H | H | CF$_3$ | H | H | NH | CH$_2$ | 1 | 18 | 41 | 2.27 |
| 14 | H | H | CH$_3$ | H | H | NH | CH$_2$ | 2 | 13 | 42 | 3.23 |
| 15 | H | CH$_3$ | H | CH$_3$ | H | NH | CH$_2$ | 2 | 19 | 70 | 3.68 |
| 16 | H | H | isopropyl | H | H | NH | CH$_2$ | 1 | 19 | 27 | 1.42 |

R$_1$, R$_2$, R$_3$, R$_4$, R$_5$, X and Z as used in this Table relate to the general structure illustrated in FIG. 1.

We claim:

1. A compound having the following structural formula:

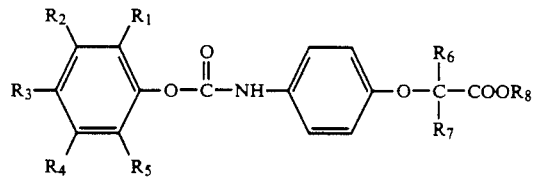

wherein R$_{1-5}$ may be hydrogen, halogen, or a substituted or unsubstituted C$_{1-3}$ alkyl group and may be the same or different, wherein R$_{6-7}$ may each be hydrogen or methyl and may be the same or different, and wherein R$_8$ may be hydrogen, a substituted or unsubstituted C$_{1-3}$ alkyl group, or a salt cation.

2. A compound having the following structural formula:

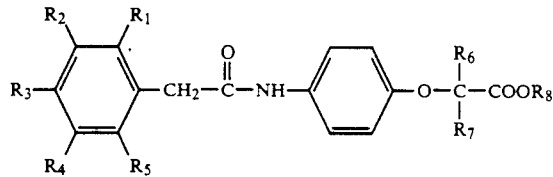

wherein R$_{1-5}$ may each by hydrogen, halogen or a substituted or unsubstituted C$_{1-3}$ alkyl group and may be the same or different, wherein $R_{6-7}$ may each be hydrogen or methyl and may be the same or different, and wherein $R_8$ may be hydrogen, a substituted or unsubstituted $C_{1-3}$ alkyl group, or a salt cation.

3. A compound having the following structural formula:

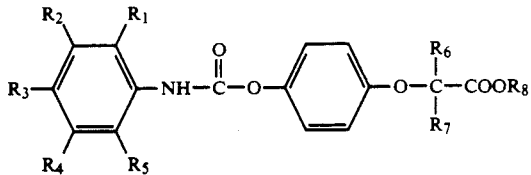

wherein $R_{1-5}$ may each be hydrogen, halogen or a substituted or unsubstituted $C_{1-3}$ alkyl group and may be the same or different, wherein $R_{6-7}$ may each be hydrogen or methyl and may be the same or different, and wherein $R_8$ may be hydrogen, a substituted or unsubstituted $C_{1-3}$ alkyl group, or a salt cation.

* * * * *

UNITED STATES PATENT AND TRADEMARK OFFICE
CERTIFICATE OF CORRECTION

PATENT NO. : 5,049,695

DATED : September 17, 1991

INVENTOR(S) : Abraham et al

It is certified that error appears in the above-identified patent and that said Letters Patent is hereby corrected as shown below:

Insert the following paragraph in column 1, after line 2:

This invention was made with governmental support under Grant HL-32973 awarded by the National Institutes of Health. The government has certain rights in the invention.

Signed and Sealed this

Thirtieth Day of March, 1993

Attest:

STEPHEN G. KUNIN

Attesting Officer

Acting Commissioner of Patents and Trademarks